United States Patent [19]

Beller et al.

[11] Patent Number: 5,698,755
[45] Date of Patent: Dec. 16, 1997

[54] PROCESS FOR PREPARING AROMATIC OLEFINS USING PALLADACYCLE CATALYSIS

[75] Inventors: Matthias Beller, Niedernhausen; Hartmut Fischer, Hofheim; Wolfgang Anton Herrmann, Freising; Christoph Brossmer, Frankfurt, all of Germany

[73] Assignee: Hoechst AG, Frankfurt, Germany

[21] Appl. No.: 493,359

[22] Filed: Jun. 21, 1995

[30] Foreign Application Priority Data

Jun. 22, 1994 [DE] Germany .................. 44 21 730.7

[51] Int. Cl.⁶ .................................................. C07C 2/68
[52] U.S. Cl. .................. 585/466; 585/435; 585/469
[58] Field of Search ....................... 585/435, 469, 585/466; 560/204; 558/371

[56] References Cited

U.S. PATENT DOCUMENTS

| | | | |
|---|---|---|---|
| 3,922,299 | 11/1975 | Heck | 585/435 |
| 4,335,055 | 6/1982 | Blaser | 560/102 |
| 4,564,479 | 1/1986 | Spencer | 560/104 |
| 5,334,750 | 8/1994 | Kaufmann et al. | 560/104 |
| 5,516,932 | 5/1996 | Beller et al. | 560/104 |
| 5,536,870 | 7/1996 | Wu | 585/435 |

FOREIGN PATENT DOCUMENTS 0 564 919  10/1993  European Pat. Off. .

OTHER PUBLICATIONS

Chemical Abstracts, vol. 101, No. 12, Sep. 17, 1984, Abstract No. 101670c, Bd. 3, Nr. 9, 1984, pp. 1414–1417.

*Primary Examiner*—Gary P. Straub
*Attorney, Agent, or Firm*—Connolly & Hutz

[57] ABSTRACT

The invention relates to a process for preparing monofunctional, bifunctional or polyfunctional aromatic olefins of the formula (I)

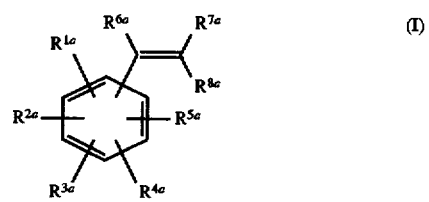

by reaction of haloaromatics of the formula (II)

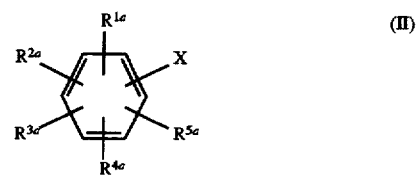

with olefins of the formula (III)

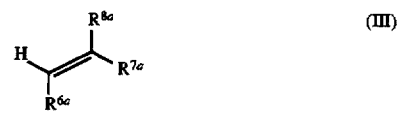

, wherein a palladium compound of the formula (IV)

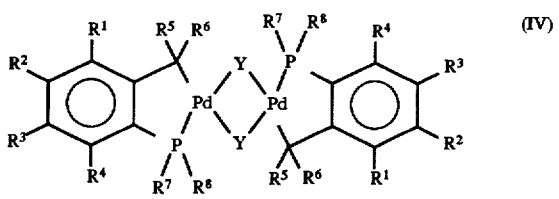

is used as the catalyst.

19 Claims, No Drawings

PROCESS FOR PREPARING AROMATIC OLEFINS USING PALLADACYCLE CATALYSIS

DESCRIPTION

Process for preparing aromatic olefins using palladacycle catalysis

The present invention relates to a new process for preparing aromatic olefins using novel catalysts, so-called palladacycles.

Aromatic olefins, in particular cinnamic acid derivatives, styrenes, stilbenes have industrial importance as fine chemicals, starting materials for polymers, UV absorbers and precursors of active compounds.

A frequently used method of synthesizing aromatic olefins in universities is the Heck reaction in which iodo-or bromoaromatics and, in exceptional cases, chloroaromatics are reacted with olefins in the presence of palladium catalysts. Overviews describing this methodology are given in, for example, R. F. Heck, Acc. Chem. Res. 1979, 12, 146; R. F. Heck, Org. React. 1982, 27, 345; R. F. Heck, Palladium Reagents in Synthesis, Academic Press, London 1985.

Catalysts used for the purposes of the Heck reaction are palladium compounds. Although both palladium(II) and palladium(0) complexes are used in Heck reactions, it is generally accepted that only palladium(0) compounds are the actual catalysts of the reaction. In particular, there are formulated in the literature coordinatively unsaturated 14-electron palladium(0) species which are generally stabilized with weak donor ligands such as phosphanes.

Despite the numerous publications on the subject of the Heck reaction, no examples of an industrial implementation of the methodology have been known hitherto. This can be attributed to the fact that the catalyst systems described frequently give satisfactory catalytic turnover numbers only with uneconomical starting materials such as iodoaromatics. Otherwise, in the case of bromoaromatics and, in particular, in the case of chloroaromatics, generally large amounts of catalyst, usually 1–5 mol %, have to be added to achieve industrially useful conversions. In addition, owing to the complexity of the reaction mixtures, no simple catalyst recycling is possible, so that the catalyst costs too generally stand in the way of industrial implementation.

There was therefore a great need for a process which does not have the specified disadvantages, is suitable for use in industry and gives aromatic olefins in high yield and purity.

This object is achieved by a process for preparing monofunctional, bifunctional or polyfunctional aromatic olefins of the formula (I)

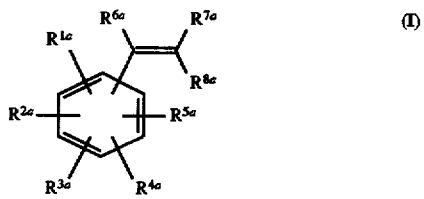

where $R^{1a}$ to $R^{5a}$ are, independently of one another, hydrogen, $C_1$–$C_8$-alkyl, alkoxy- ($C_1$–$C_8$), acyloxy-($C_1$–$C_8$), O-phenyl, phenyl, fluorine, chlorine, bromine, iodine, OH, $NO_2$, $OSO_2CF_3$, CN, COOH, CHO, $SO_3H$, $SO_2R$, SOR, $NH_2$, NH-alkyl-($C_1$–$C_8$), N-alkyl$_2$-($C_1$–$C_8$), CHal$_3$, NHCO-alkyl-($C_1$–$C_4$), N-alkyl-($C_1$–$C_4$)-CO-alkyl-($C_1$–$C_4$), COO-alkyl-($C_1$–$C_8$), CONH$_2$, CO-alkyl-($C_1$–$C_8$), NHCOH, NCOO-alkyl-($C_1$–$C_4$), CO-phenyl, COO-phenyl, CHCH-$CO_2$-alkyl-($C_1$–$C_8$), CHCHCO$_2$H, PO-phenyl$_2$, PO-alkyl$_2$-($C_1$–$C_4$), where one of the radicals $R^{1a}$ to $R^{5a}$ can also be

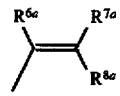

$R^{6a}$ is hydrogen, alkyl ($C_1$–$C_8$), phenyl, O-alkyl-($C_1$–$C_8$), fluorine, $R^{7a}$ and $R^{8a}$ are, independently of one another, hydrogen, CN, $CO_2H$, $CO_2$-alkyl- ($C_1$–$C_8$), $CONH_2$, CONH-alkyl-($C_1$–$C_4$), CON(alkyl)$_2$-($C_1$–$C_4$), fluorine, $CO_2$-phenyl, alkyl, ($C_1$–$C_8$)-phenyl, PO(phenyl), PO(alkyl-($C_1$–$C_4$))$_2$, CO-phenyl, CO-alkyl-($C_1$–$C_4$), O-alkyl-($C_1$–$C_4$), NH-alkyl-($C_1$–$C_4$), $PO_3H$, $SO_3H$, $SO_3$-alkyl-($C_1$–$C_4$), $SO_2$-alkyl-($C_1$–$C_4$), O-phenyl, by reaction of haloaromatics of the formula (II)

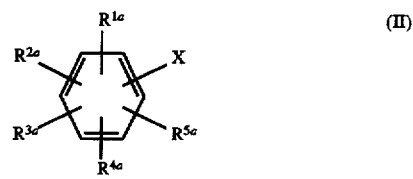

with olefins of the formula (III)

where $R^{1a}$ to $R^{8a}$ are as defined above, where one of the radicals $R^{1a}$ to $R^{5a}$ can also be X and X is iodine, bromine, chlorine, $OSO_2CF_3$, $OSO_2$-phenyl, $OSO_2CH_3$, wherein a palladium compound of the formula (IV)

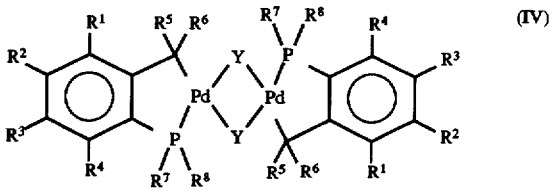

where $R^1$, $R^2$, $R^3$, $R^4$, $R^5$, $R^6$ are, independently of one another, hydrogen, ($C_1$–$C_4$) -alkyl, ($C_5$–$C_8$)-cycloalkyl, ($C_1$–$C_4$)-alkoxy, fluorine, $NH_2$, NH-alkyl ($C_1$–$C_4$), N(alkyl)$_2$-($C_1$–$C_4$), $CO_2$alkyl-($C_1$–$C_4$), OCO-alkyl-($C_1$–$C_4$) or phenyl, or $R^1$ and $R^2$, $R^2$ and $R^3$, $R^3$ and $R^4$, $R^5$ and $R^6$ together form an aliphatic or aromatic ring, and $R^7$, $R^8$ are ($C_1$–$C_8$)-alkyl, ($C_3$–$C_{12}$)-cycloalkyl, substituted or unsubstituted aryl and Y is an anion of an inorganic or organic acid, is used as catalyst.

In many cases, compounds of the formula (IV) in which $R^1$ to $R^6$ are hydrogen, alkyl($C_1$–$C_4$), phenyl, cycloalkyl-($C_5$–$C_8$), $R^7$ and $R^8$ are phenyl, tolyl, xylyl, mesityl, alkyl ($C_1$–$C_8$) and cycloalkyl($C_5$–$C_8$) and Y is acetate, propionate, benzoate, chloride, bromide, iodide, fluoride, sulfate, hydrogensulfate, nitrate, phosphate, tetrafluoroborate, tosylate, mesylate, acetylacetonate, hexafluoroacetylacetonate or pyrazolyl have been found to be useful.

Well suited compounds are, for example, those in which $R^1$–$R^6$ are H, alkyl, phenyl and $R^7$, $R^8$ are alkyl, phenyl, tolyl, mesityl and xylyl.

Very good results are given by the compounds:

trans-di-μ-acetato-bis[o-(di-o-tolylphosphino)benzyl]-dipalladium (II)

trans-di-μ-chloro-bis[o-(di-o-tolylphosphino)benzyl]-dipalladium (II)

trans-di-μ-bromo-bis[o-(di-o-tolylphosphino)benzyl]-dipalladium (II)

trans-di-μ-iodo-bis[o-(di-o-tolylphosphino)benzyl]dipalladium(II)

trans-di-μ-acetato-bis[o-(dimesitylphosphino)-3,5-dimethylbenzyl]dipalladium (II)

trans-di-μ-chloro-bis[o-(dimesitylphosphino)-3,5-dimethylbenzyl]dipalladium (II)

trans-di-μ-bromo-bis[o-(dimesitylphosphino)-3,5-dimethylbenzyl]dipalladium (II)

trans-di-μ-iodo-bis[o-(dimesitylphosphino)-3,5-dimethylbenzyl]dipalladium (II)

trans-di-μ-acetato-bis[o-(t-butyl-o-tolylphosphino)-benzyl]dipalladium (II)

trans-di-μ-acetato-bis[o-(di-t-butylphosphino)benzyl]-dipalladium (II)

trans-di-μ-acetato-bis[o-(cyclohexyl-o-tolylphosphino)-benzyl]dipalladium (II)

The process has been found to be particularly useful for the preparation of compounds of the formula (I) in which: $R^{1a}$ to $R^{5a}$ are, independently of one another, hydrogen, ($C_1$–$C_8$)-alkyl, ($C_1$–$C_8$)-alkoxy, ($C_1$–$C_8$)-acyloxy, phenyl, fluorine, chlorine, $NO_2$, CN, COOH, CHO, $SO_2R$, NH—($C_1$–$C_8$)-alkyl, N[($C_1$–$C_8$) alkyl]$_2$, COO-($C_1$–$C_8$)-alkyl, $CONH_2$, CO-($C_1$–$C_8$)-alkyl, CO-phenyl, COO-phenyl, PO-(phenyl)$_2$, $R^{6a}$ is hydrogen, ($C_1$–$C_8$)-alkyl, $R^{7a}$, $R^{8a}$ are, independently of one another, hydrogen, CN, $CO_2H$, $CO_2$-($C_1$–$C_8$)-alkyl, $CO_2$-phenyl, ($C_1$–$C_8$)-alkyl, CO-phenyl, CO-($C_1$–$C_4$)-alkyl.

The process is important, for example, for preparing compounds of the formula (I) in which:
$R^{1a}$ to $R^{5a}$ are, independently of one another, hydrogen, ($C_1$–$C_8$)-alkyl, ($C_1$–$C_8$)-alkoxy, phenyl, fluorine, chlorine, $NO_2$, CN, COOH, CHO, COO-($C_1$–$C_8$)-alkyl, $CONH_2$, CO-($C_1$–$C_8$)-alkyl, CO-phenyl, PO-(phenyl)$_2$, $R^{6a}$ is hydrogen, $R^{7a}$, $R^{8a}$, are, independently of one another, CN, $CO_2H$, $CO_2$-($C_1$–$C_8$)-alkyl, $CO_2$-phenyl, CO-phenyl, CO-($C_1$–$C_4$)-alkyl.

Solvents used are generally inert organic solvents. Well suited solvents are dipolar aprotic solvents such as dialkyl sulfoxides, N,N-dialkylamides of aliphatic carboxylic acids or alkylated lactams. Here, preference is given to dimethyl sulfoxide, dimethylacetamide, dimethylformamide and N-methylpyrrolidone.

The reaction proceeds at temperatures of from 20° to 200° C., in many cases it has been found to be useful to carry out the reaction at temperatures of from 60° to 180° C., preferably from 100° to 150° C.

Since HX is eliminated in the reaction, it is advantageous to neutralize this acid by adding a base. Suitable bases for this purpose are primary, secondary or tertiary amines such as alkylamines, dialkylamines, trialkylamines, which can be alicyclic or open-chain, and alkali metal or alkaline earth metal salts of aliphatic or aromatic carboxylic acids or carbonic acid, such as lithium, sodium, potassium, calcium, magnesium acetate and corresponding carbonates or hydrogencarbonates.

The palladium catalysts used are generally synthesized separately prior to the actual reaction, but they can also be generated in situ without the initial catalytic activity being reduced thereby. However, if the reaction is relatively prolonged, the mixtures prepared in situ (molar ratio Pd: P=1:1) prove to be not very stable and frequently lead to precipitation of palladium. Therefore, in the case of in situ mixtures, it is necessary to work with an excess of phosphane which is not needed when the palladacycles are used.

The synthesis of the palladium catalysts used is carried out according to the process of the German Patent Application P 44 21 753.6 filed on the same day which corresponds to U.S. application Ser. No. 08/493,147.

The palladacycles used or formed generally have a dimeric structure. However, in the case of certain compounds (e.g. Y=acetylacetone, hexafluoroacetylacetone), monomeric, oligomeric or even polymeric structures can also be present.

During the catalysis cycle, the dimeric structure is broken up by bridge-cleavage reactions with inorganic and organic nucleophiles, so that the actual catalytically active species are to be considered to be the mononuclear complexes of the formula (V) or (VI)

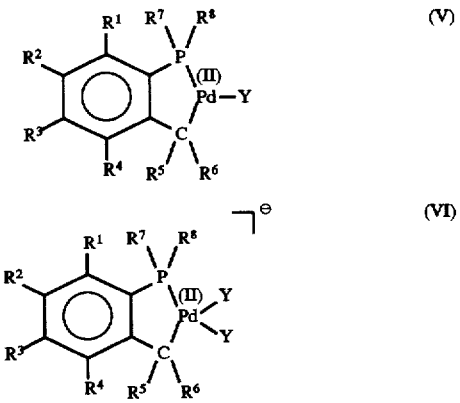

The complexes of the formulae (V) and (VI) are in equilibrium with the dimers actually used and have a neutral or anionic character. The mononuclear complex of the formula (V) may here contain further donor ligands on the palladium atom.

The very advantageous course of the reaction of the invention was particularly surprising since according to the prior art palladium catalysts of the formula (IV) were considered as unsuitable for carrying out the Heck reaction.

Thus, R. F. Heck expressly states that palladacycles possess no catalytic activity for the arylation of olefins (T. Mitsudo, W. Fischetti, R. F. Heck, J. Org. Chem., 1984, vol. 49, 1640).

A. L. Rheingold and W. C. Fultz too (Organometallics, 1984, vol. 3, 1414) described that the Heck reaction of iodoaromatics with dienes in the presence of palladium acetate and tris(o-tolyl)phosphane forms palladacycles which have no catalytic activity.

In view of this background, the advantages of the catalysts used in the processes of the invention are most unexpected and particularly surprising.

The palladacycles used as novel catalyst systems have a very high activity combined, unexpectedly, with accompanying high stability.

The stability of the palladacycles in solution can be increased by addition of alkali metal salts, alkaline earth metal salts and transition metal salts of transition groups VI to VIII. In particular, the addition of halides and pseudo halides (e.g. CN$^-$) effects, in the reaction of chloroaromatics, significant yield increases (from 1 to 100%) and improvements in the operating life of the homogeneous catalyst. Suitable salts are also trialkyl ammonium and tetraalkyl ammonium salts and corresponding phosphonium and arsonium salts.

Turnover numbers of the order of 1000,000 and more can thus be realized.

Owing to the catalyst activities and stability it is thus possible, for certain processes, to use extremely small amounts of catalyst, so that the catalyst costs are, in comparison with conventional Heck reactions, not cost-limiting for the corresponding process.

Furthermore, the use of very minimal amounts of catalyst gives ecological advantages, since waste products or workup processes for waste products are avoided.

The following examples serve to illustrate the process of the invention, without restricting it to them.

EXAMPLE 1

Synthesis of the Catalyst

1. Trans-Di-µ-acetato-bis[o-(di-o-tolylphosphino)-benzyl]palladium(II) (1)

4.5 g (20 mmol) of Pd(OAc)$_2$ are dissolved in 500 ml of toluene, giving a reddish brown coloration. The solution is admixed with 8.0 g (26.3 mmol) of tri (o-tolyl) phosphane. The solution, which rapidly becomes clear and light orange in color, is heated for 3 minutes at barely 50° C. and then cooled to room temperature. The solvent is removed in vacuo to ¼ of the volume. After addition of 500 ml of hexane, the precipitated form is filtered off. This gives 8.8 g (93% of theory, based on Pd(OAc)$_2$) of (1) as a yellow solid (mp>200° C.). (1) can be isolated in analytically pure form as yellow crystalline needles by recrystallization from toluene/hexane or methylene chloride/hexane and filtration of the solutions through Celite®.

Elemental analysis:
Found: C, 58.89%; H, 5.06%; P, 6.92%; O, 6.47%; Pd, 21.84%; C$_{46}$H$_{46}$O$_4$P$_2$Pd$_2$ (937.62)
calc.: C, 58.93%; H, 4.94%; P, 6.61%; O, 6.83%; Pd, 22.70%; IR (cm$^{-1}$, KBr): 3052m, 3007m, 2954w, 2925m ν(CH); 1578vs ν(µ$_2$-C=O), 1468s; 1630 ν (C=C); 1578, 1416 ν/µ$_2$-CO); 1341;

$^1$H-NMR (400 MHz, −70° C., CD$_2$Cl$_2$): δ=7.31 (4H, m, H$_{Tolyl}$); 7.21 (2H, m, H$_{Tolyl}$); 7.12 (6H, m, H$_{Tolyl}$); 7.06 (2H, t, H$_{Benzyl}$, $^3$J(HH)=7.3 Hz); 6.92 (4H, m, H$_{Tolyl}$); 6.70 (2H, t, H$_{Benzyl}$, $^3$J(HH)=7.3 Hz); 6.56 (2H, t, H$_{Benzyl}$, $^3$J(HH)=9 Hz); 6.35 (2H, dd, H$_{Benzyl}$, $^3$J(HH)=7.9 Hz, $^4$J(PH)=12.2 Hz); 3.00 (6H, s, CH$_3$); 2.81 (2H, dd, CH$_a$H$_b$, $^2$J(H$_a$H$_b$)= 14.0 Hz, $^3$J(PH)=4.3 Hz); 2.40 (2H, dd, CH$_a$H$_b$, $^2$J(H$_a$H$_b$) =14.0 Hz, $^3$J(PH)=1.8 Hz); 2.10 (6H, s, CH$_3$); 1.91 (s, 6H, CH$_3$);

$^{13}$C{$^1$H}-NMR (100.5 MHz, −70° C., CD$_2$Cl$_2$): δ=178.5 (s, CH$_3$CO$_2$); 157.1 (d, C$_{Ar}$, J(PC)=31.3 Hz); 141.1 (d, C$_{Ar}$, J(PC) =16.0 Hz); 141.0 (d, C$_{Ar}$, J(PC)=21.0 Hz); 133.0 (S, C$_{Ar}$); 132.5 (d, C$_{Ar}$, J(PC)=4.6 Hz); 132.4 (d, C$_{Ar}$, J(PC)=6.1 Hz); 131.7 (d, C$_{Ar}$, J(PC)=8.8 Hz); 131.4 (d, C$_{Ar}$; J(PC)= 13.7); 131.3 (d, C$_{Ar}$, J(PC)=9.9 Hz); 130.4 (d, C$_{Ar}$, J(PC)= 16.0 Hz); 129.9 (s, C$_{Ar}$); 129.1 (d, C$_{Ar}$, J(PC)=46.2 Hz); 128.7 (S, C$_{Ar}$); 128.1 (d, C$_{Ar}$, J(PC)=33.2 Hz); 127.6 (d, C$_{Ar}$, J(PC)=23.7 Hz); 125.6 (d, C$_{Ar}$, J(PC)=7.3 Hz); 125.2 (d, C$_{Ar}$, J(PC)=7.3 HZ); 124.9 (d, C$_{Ar}$, J(PC)=11.4 Hz); 30.8 (s, CH$_2$); 24.7 (d, CH$_3$CO$_2$, 4J(PC)=3.1 Hz); 23.0 (d, CH$_3$, 3J(PC)=13.7 Hz); 2.2 (d, CH$_3$, 3J(PC)=6.9 Hz);

$^{31}$P{$^1$H}-NMR (161.9 MHz, −70° C., CD2C12): δ=34.2 (s); CI-MS (150 eV): m/e=939 [M$^+$+H], 880 [M$^+$-OAc], 819 [M$^+$-2OAc], 714 [Pd{o-CH$_2$C$_6$H$_4$P (o-Tol)$_2$}$_2^+$].

EXAMPLE 2

100 mmol of 4-bromobenzaldehyde, 170 mmol of n-butyl acrylate, 100 mmol of sodium acetate are stirred in 100 ml of dimethylacetamide with 0.005 mmol of trans-di-µ-acetato-bis [o-(di-o-tolylphosphino)benzyl]-dipalladium(II) as catalyst for 3 hours at 130° C.

Yield: 100% of n-butyl 4-formylcinnamate.

EXAMPLE 3

100mmol of 4-bromoacetophenone, 150 mmol of 2-ethylhexyl acrylate, 110 mmol of sodium acetate are stirred in 100 mmol of dimethylacetamide with 0.005 mmol of trans-di-µ-acetato-bis[o-(di-o-tolylphosphino)benzyl]-dipalladium(II) as catalyst for 3 hours at 130° C.

Yield: 100% of 2-ethylhexyl E-4-acetylcinnamate.

EXAMPLE 4

100 mmol of 4-chloroacetophenone, 170 mmol of 2-ethylhexyl acrylate, 110 mmol of sodium acetate, 10 mmol of lithium bromide are stirred in 100 mmol of dimethylacetamide with 0.05 mmol of trans-di-µ-acetato-bis[o-(di-o-tolylphosphino)benzyl]dipalladium(II) as catalyst for 18 hours at 130° C.

Yield: 82% of 2-ethylhexyl E-4-acetylcinnamate.

EXAMPLE 5

100 mmol of 2-bromotoluene, 170 mmol of n-butyl acrylate, 110 mmol of sodium acetate, are stirred in 100 ml of dimethylacetamide with 1 mmol of trans-di-µ-acetato-bis [o-(di-o-tolylphosphino) benzyl]dipalladium (II) as catalyst for 48 hours at 140° C.

Yield: 92% of butyl E-2-methylcinnamate.

EXAMPLE 6

100 mmol of bromobenzene, 170 mmol of butyl acrylate, 110 mmol of sodium acetate, are stirred in 100 ml of dimethylacetamide with i mmol of trans-di-µ-acetato-bis[o-(di-o-tolylphosphino)benzyl]dipalladium(II) as catalyst for 48 hours at 140° C.

Yield: 96% of butyl cinnamate.

EXAMPLE 7

100mmol of 4-bromoacetophenone, 150 mmol of 2-ethylhexyl acrylate, 110 mmol of sodium acetate are stirred in 100 ml of dimethylacetamide with 0.005 mmol of trans-di-µ-acetato-bis[o-(diphenylphosphino)-4-methylbenzyl]-dipalladium(II) as catalyst for 3 hours at 130° C.

Yield: 100% of 2-ethylhexyl 4-acetyl cinnamate.

EXAMPLE 8

1.00 mmol of 4-iodobromobenzene, 3.0 mmol of n-butyl acrylate, 2.2 mmol of sodium acetate are stirred in 10 ml of dimethylacetamide with 0.005 mmol of di-µ-acetato-bis[o-(di-o-tolylphosphino)benzyl]dipalladium(II) as catalyst for 48 hours at 140° C.

Yield: 85% of (E,E')-1,4-bis(2-butoxycarbonylvinyl)-benzene.

EXAMPLE 9

100 mmol of 4-bromobenzaldehyde, 150 mmol of butyl acrylate, 110 mmol of sodium acetate are stirred in 80 ml of dimethylacetamide with 0.001 mmol of trans-di-µ-acetato-bis[o-(dimesitylphosphino)-3,5-dimethylbenzyl]-dipalladium(II) for 6 hours at 135° C.

Yield: 99% of butyl 4-formylcinnamate.

EXAMPLE 10

100 mmol of 4-bromobenzaldehyde, 150 mmol of butyl acrylate, 110 mmol of sodium acetate are stirred in 80 ml of dimethylacetamide with 0.001 mmol of trans-di-μ-acetato-bis[o-(t-butyl-o-tolylphosphino)benzyl]-dipalladium(II) for 6 hours at 135° C.
Yield: 100% of butyl 4-formylcinnamate.

EXAMPLE 11

100 mmol of 4-bromobenzaldehyde, 150 mmol of butyl acrylate, 110 mmol of sodium acetate are stirred in 100 ml of dimethylacetamide with 0.001 mmol of trans-di-μ-acetato-bis [o-(di-t-butylphosphino)benzyl]-dipalladium(II) for 6 hours at 130° C.
Yield: 100% of butyl 4-formylcinnamate.

EXAMPLE 12

100 mmol of 4-bromobenzaldehyde, 150 mmol of butyl acrylate, 110mmol of sodium acetate are stirred in 80 ml of dimethylacetamide with 0.001 mmol of trans-di-μ-acetato-bis[o-cyclohexyl-o-tolylphosphino)benzyl]-dipalladium(II) for 4 hours at 135° C.
Yield: 100% of butyl 4-formylcinnamate.

EXAMPLE 13

100 mmol of 4-bromobenzaldehyde, 150 mmol of butyl acrylate, 110mmol of sodium acetate are stirred in 80 ml of dimethylacetamide with 0.001 mmol of trans-di-μ-bromo-bis[o(dimesitylphosphino)-3,5-dimethylbenzyl]dipalladium (II) for 4 hours at 135° C.
Yield: 98% of butyl 4-formylcinnamate.

EXAMPLE 14

100 mmol of 4-bromobenzaldehyde, 150 mmol of butyl acrylate, 110mmol of sodium acetate are stirred in 80 ml of dimethylacetamide with 0.001 mmol of trans-di-μ-bromo-bis[o-(di-o-tolylphosphino)benzyl]dipalladium(II) for 6 hours at 140° C.
Yield: 100% of butyl 4-formylcinnamate.

EXAMPLE 15

100 mmol of 4-bromobenzaldehyde, 180 mmol of styrene, 110 mmol of sodium acetate are stirred in 80 ml of dimethylacetamide with 0.1 mmol of trans-di-μ-bromo-bis [o-(di-o-tolylphosphino)benzyl]dipalladium(II) for 6 hours at 140° C.
Yield: 96% of 4-formylstilbene.

EXAMPLE 16

100 mmol of 4-bromoanisole, 150 mmol of butyl acrylate, 110 mmol of sodium acetate are stirred in 80 ml of dimethylacetamide with 0.1 mmol of trans-di-μ-acetato-bis[o-(cyclohexyl-o-tolylphosphino)benzyl]dipalladium(II) for 4 hours at 145° C.
Yield: 94% of butyl 4-methoxycinnamate.

EXAMPLE 17

100 mmol of 4-bromoanisole, 150 mmol of butyl acrylate, 110 mmol of sodium acetate are stirred in 80 ml of dimethylacetamide with 0.1 mmol of trans-di-μ-iodo-bis[o-(cyclohexyl-o-tolylphosphino)benzyl]dipalladium(II) for 4 hours at 145° C.
Yield: 87% of butyl 4-methoxycinnamate.

EXAMPLE 18

25 mmol of bromoacetophenone, 37 mmol of styrene, 30 mmol of sodium acetate, 0.60 g of bis(di-o-tolylphosphino-benzyl)palladium acetate and 2 mg of di-tert-butylphenol are stirred in 50 ml of dimethylacetamide at 130° C. until reaction is complete. After filtering off the salts, precipitation of the crude product with water and recrystallization from acetone/water, this gives 87% of product.
Yield: 87% of 4-acetylstilbene.

EXAMPLE 19

310 mmol of 1-bromo-2,4-difluorobenzene, 465 mmol of butyl acrylate, 372 mmol of sodium acetate are stirred in 150 ml of dimethylacetamide with 0.31 mol of bis(di-o-tolylphosphinobenzyl)palladium acetate for 16 hours at 130° C.
Yield: 82% of butyl 2,4-difluorocinnamate.

EXAMPLE 20

20 mmol of 4-bromonitrobenzene, 40 mmol of butyl vinyl ether, 30 mmol of triethylamine are stirred in 20 ml of xylene with 0.2 mmol of bis(di-o-tolylphosphinobenzyl)-palladium acetate for 16 hours at 140° C.
Conversion: 100%
Selectivity: 9:1=2-(cis,trans)-butoxy-1-(4-nitrophenyl)ethylene/1-butoxy-1-(4-nitrophenyl)ethylene.

We claim:
1. A high yield process for preparing monofunctional, bifunctional or polyfunctional aromatic olefins of the formula (I)

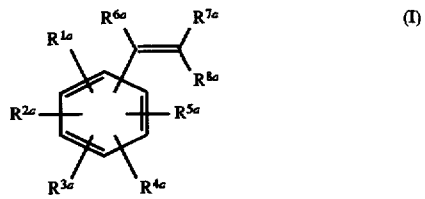

where
$R^{1a}$ to $R^{5a}$ are, independently of one another, hydrogen, $C_1$–$C_8$-alkyl, akoxy-($C_1$–$C_8$), acyloxy-($C_1$–$C_8$), O-phenyl, phenyl, fluorine, chlorine, bromine, iodine, OH, $NO_2$, $OSO_2CF_3$, CN, COOH, CHO, $SO_3H$, $SO_2R$, SOR, $NH_2$, NH-alkyl-($C_1$–$C_8$), N-alkyl$_2$-($C_1$–$C_8$), $CHal_3$, NHCO-alkyl-($C_1$–$C_4$), N-alkyl-($C_1$–$C_4$)-CO-alkyl-($C_1$–$C_4$), COO-alkyl-($C_1$–$C_8$), $CONH_2$, CO-alkyl-($C_1$–$C_8$), NHCOH, NCOO-alkyl-($C_1$–$C_4$), CO-phenyl, COO-phenyl, CHCH-$CO_2$-alkyl-($C_1$–$C_8$), $CHCHCO_2H$, PO-phenyl$_2$ or PO-alkyl$_2$-($C_1$–$C_4$), where one of the radicals $R^{1a}$ to $R^{5a}$ can also be

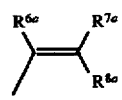

$R^{8a}$ is hydrogen, alkyl ($C_1$–$C_8$), phenyl, O-alkyl-($C_1$–$C_8$) or fluorine, $R^{7a}$ and $R^{8a}$ are, independently of one another, hydrogen, CN, $CO_2H$, $CO_2$-alkyl-($C_1$–$C_8$), $CONH_2$, CONH-alkyl-($C_1$–$C_4$), CON(alkyl)$_2$-($C_1$–$C_4$), fluorine, $CO_2$-phenyl, alkyl, ($C_1$–$C_8$)-phenyl, PO(phenyl), PO(alkyl-($C_1$–$C_4$))$_2$, CO-phenyl, CO-alkyl-($C_1$–$C_4$), O-alkyl-($C_1$–$C_4$), NH-alkyl-($C_1$–$C_4$), $PO_3H$, $SO_3H$, $SO_3$-alkyl-($C_1$–$C_4$), $SO_2$-alkyl-($C_1$–$C_4$) or O-phenyl, by reaction of haloaromatics of the formula (II)

with olefins of the formula (II)

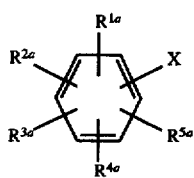

with olefins of the formula (III)

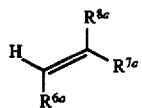

where $R^{1a}$ to $R^{8a}$ are as defined above, wherein one of the radicals $R^{1a}$ to $R^{5a}$ can also be X and X is iodine, bromine, chlorine, $OSO_2CF_3$, $OSO_2$-phenyl, $OSO_2CH_3$, and providing a palladium phosphane compound of the formula (IV) as a catalyst,

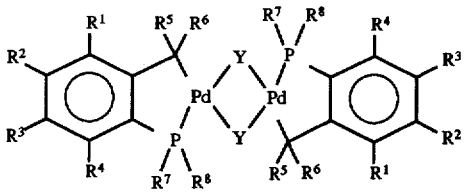

where
- $R^1$, $R^2$, $R^3$, $R^4$, $R^5$ and $R^6$ are, independently of one another, hydrogen, $(C_1-C_4)$-alkyl, $(C_3-C_8)$-cycloalkyl, $(C_1-C_4)$-alkoxy, fluorine, $NH_2$, $NH$-alkyl$(C_1-C_4)$, $N(alkyl)_2$-$(C_1-C_4)$, $CO_2$alkyl-$(C_1-C_4)$, $OCO$-alkyl-$(C_1-C_4)$ or phenyl,
- or $R^1$ and $R^2$, $R^2$ and $R^3$, $R^3$ and $R^4$, $R^5$ and $R^6$ together form aliphatic or aroma and $R^7$ and $R^8$, independently of one another, $R^8$ are $(C_1-C_8)$-alkyl, $(C_3-C_{12})$-cycloalkyl, substituted or unsubstituted aryl and
- Y is an anion of an inorganic or organic acid and wherein the palladium to phosphane ratio in the system is about 1:1.

2. The process as claimed in claim 1, wherein, in formula (IV), $R^1$ to $R^6$ are, independently of one another, hydrogen, $(C_1-C_4)$-alkyl or $(C_5-C_8)$-cycloalkyl, $R^7$ and $R^8$, independently of one another, are phenyl, tolyl, xylyl, mesityl, alkyl-$(C_1-C_8)$ or cycloalkyl-$(C_5-C_8)$ and
Y is acetate, propionate, benzoate, chloride, bromide, iodide, fluoride, sulfate, hydrogensulfate, nitrate, phosphate, tetrafluoroborate, tosylate, mesylate, acetylacetonate, hexafluoroacetylacetonate or pyrazolyl.

3. The process as claimed in claim 1, wherein the catalyst is prepared in situ.

4. The process as claimed in claim 1, wherein in formula (I):
$R^{1a}$ to $R^{5a}$ are, independently of one another, hydrogen, $(C_1-C_8)$-alkyl, $(C_1-C_8)$-alkoxy, phenyl, fluorine, chlorine, $NO_2$, CN, COOH, CHO, COO-$(C_1-C_8)$-alkyl, $CONH_2$, CO-$(C_1-C_8)$-alkyl, CO-phenyl or PO-(phenyl)$_2$,
$R^{6a}$ is hydrogen,
$R^{7a}$ $R^{8a}$, are, independently of one another, CN, $CO_2H$, $CO_2$-$(C_1-C_8)$-alkyl, $CO_2$-phenyl, CO-phenyl or CO-$(C_1-C_4)$-alkyl.

5. The process as claimed in claim 1, wherein solvents used are dipolar aprotic solvents.

6. The process as claimed in claim 5, wherein said solvents are dialkyl sulfoxides, N,N-dialkylamides or alkylated lactams.

7. The process as claimed in claim 5, wherein said solvents are dimethylsulfoxide, dimethylacetamide, dimethylformaide or N-methylpyrrolidone.

8. The process as claimed in claim 1, wherein the reaction is carried out at temperature of from 20° to 200° C.

9. The process as claimed in claim 8, wherein the reaction is carried out at a temperature from 60° to 180° C.

10. The process as claimed in claim 8, wherein the reaction is carried out at temperature of from 100° to 150° C.

11. The process as claimed in claim 1, wherein an acid HX is formed in the reaction and is neutralized by adding a base.

12. The process as claimed in claim 11, wherein the base used is an alkylamine, carbonate, hydrogencarbonate or acetate of lithium, sodium, potassium, calcium or magnesium.

13. The process as claimed in claim 11, wherein said base is an amine, an alkyl metal salt of a weak acid or alkaline earth metal salt of a weak acid.

14. The process as claimed in claim 1, further comprising adding salts of halides and pseudohalides of the alkali metals, alkaline earth metals or metals of transition group VI to VIII.

15. The process as claimed in claim 1, further comprising adding trialkylammonium tetraalkylammonium, trialkylphosphonium tetraalkylphosphonium trialkylarsonium or tetraalkylarsonium salts.

16. The process as claimed in claim 1, wherein said catalyst is selected from the group consisting of
- trans-di-μ-acetato-bis{o-(di-o-tolylphosphino) benzyl}dipalladium(II),
- trans-di-μ-chloro-bis{o-(di-o-tolylphosphino) benzyl}dipalladium(II),
- trans-di-μbromo-bis{o-(di-o-tolylphosphino) benzyl}dipalladium(II),
- trans-diμ-iodo-bis{o-(di-o-tolylphosphino) benzyl}dipalladium(II),
- trans-di-μ-acetato-bis{o-(dimesitylphosphino)-3,5-dimethylbenzyl}dipalladium(II),
- trans-di-μ-chloro-bis{o-(dimesitylphosphino)-3,5-dimethylbenzyl}dipalladium(II),
- trans-di-μ-bromo-bis{o- (dimesitylphosphino)-3,5-dimethylbenzyl}dipalladium(II),
- trans-di-μ-iodo-bis-{o-(dimesitylphosphino)-3,5-dimethylbenzyl}dipalladinm(II),
- trans-di-μ-acetato-bis{o-(t-butyl-o-tolylphosphino)-benzyl }dipalladium(II),
- trans-di-μ-acetato-bis{o-(di-t-butylphosphino)-benzyl}dipalladium(II) and
- trans-di-μ-acetato-bis{o-(cyclohexyl-o-tolyl-phosphino) benzyl}dipalladium(II).

17. The process as claimed in claim 1, wherein, in formula (I): $R^{1a}$ to $R^{5a}$ are, independently of one another, hydrogen, $(C_1-C_8)$-alkyl, $(C_1-C_8)$-alkoxy, $(C_1-C_8)$acyloxy, phenyl, fluorine, chlorine, $NO_2$, CN, COOH, CHO, $SO_2R$, NH-$(C_1-C_8)$-alkyl, N{$(C_1-C_8)$alkyl}$_2$, COO-$(C_1-C_8)$-alkyl, $CONH_2$, CO-$(C_1-C_8)$-alkyl, CO-phenyl, COO-phenyl or PO-(phenyl)$_2$,
$R^{6a}$ is hydrogen or $(C_1-C_8)$-alkyl,
$R^{7a}$ and $R^{8a}$ are, independently of one another, hydrogen, CN, $CO_2H$, $CO_2$-$(C_1-C_8)$-alkyl, $CO_2$-phenyl, $(C_1-C_8)$-alkyl, CO-phenyl or CO-$(C_1-C_4)$-alkyl.

18. The process as claimed in claim 1, wherein the ratio of palladium to phosphane is 1:1.

19. The process as claimed in claim 1, wherein the process yields from 92 to 100% of formula 1.

* * * * *